US 6,603,315 B2

(12) United States Patent
Dahms

(10) Patent No.: US 6,603,315 B2
(45) Date of Patent: Aug. 5, 2003

(54) MEASURING PROBE, MEASURING INSTRUMENT AND METHOD FOR DETERMINING THE PHYSICAL STABILITY OF EMULSIONS AND DISPERSIONS

(75) Inventor: Gerd Dahms, Duisburg (DE)

(73) Assignee: IFAC GmbH & Co. KG, Duisburg (DE)

(*) Notice: Subject to any disclaimer, the term of this patent is extended or adjusted under 35 U.S.C. 154(b) by 0 days.

(21) Appl. No.: 09/771,949

(22) Filed: Jan. 30, 2001

(65) Prior Publication Data

US 2002/0101244 A1 Aug. 1, 2002

(51) Int. Cl.[7] .............................................. G01N 27/60
(52) U.S. Cl. ...................................... 324/455; 324/686
(58) Field of Search ................................ 324/455, 686; 702/19

(56) References Cited

U.S. PATENT DOCUMENTS

| 4,468,611 A | * | 8/1984 | Tward | 324/686 |
| 5,212,018 A | | 5/1993 | Iwamoto | 428/559 |
| 5,339,254 A | * | 8/1994 | Matlock | 702/19 |
| 5,767,682 A | * | 6/1998 | Sekimoto | 324/455 |

FOREIGN PATENT DOCUMENTS

| DE | 3006877 | * | 9/1981 |
| DE | 197 03 378 | | 8/1998 |
| DE | 200 13 089 | | 11/2000 |
| DE | 20013089 | * | 11/2000 |

OTHER PUBLICATIONS

"COSSMA Aerosol and Spray Report: Cosmetics Spray Technology Marketing", G. Braun Fachverlage, E51280, Feb. 2000, pp. 58, 42 and 43.

* cited by examiner

Primary Examiner—Christine K. Oda
(74) Attorney, Agent, or Firm—Foley & Lardner

(57) ABSTRACT

A measuring probe for determining the physical stability of emulsions and dispersions, is constructed from a rod comprising a material which is electrically nonconductive at least on the rod surface. The rod carries at least two conductivity-measurement electrodes separated from one another along the rod. These electrodes are separately supplied with electricity via the interior of the rod at one rod end. A method for determining the physical stability of emulsions and suspensions involves placing an emulsion or dispersion a sample container, immersing a measuring probe in the filled sample container, and measuring the conductivity of the emulsion or dispersion continuously or at intervals over a given period of time using the conductivity-measurement electrodes.

17 Claims, 3 Drawing Sheets

MEASURING PROBE, MEASURING INSTRUMENT AND METHOD FOR DETERMINING THE PHYSICAL STABILITY OF EMULSIONS AND DISPERSIONS

FIELD OF THE INVENTION

The invention relates to a measuring probe and to a measuring instrument, as well as to a method for determining the physical stability of emulsions and dispersions.

BACKGROUND OF THE INVENTION

Emulsions and dispersions are among the most important of industrial merchandise, and are used in a very wide variety of fields. Since the manufacturers have to guarantee a certain degree of stability for their products, a reliable and fast method for predicting the stability of emulsions and dispersions would be of interest to them.

To date, the most widespread method for determining the physical stability of emulsions and dispersions has involved visual assessment of the samples by a person skilled in the art during storage in air-conditioned cabinets. The disadvantages of this method include the long delay between the time when the samples are produced and the time when precipitation can first be detected by eye, the degree to which the assessment depends on the particular person skilled in the art carrying out the examination, and the fact that the result lacks quantifiability. Furthermore, slight de-mixing or phase segregation in emulsions and dispersions cannot be picked up visually.

SUMMARY OF THE INVENTION

One object of the present invention is to provide a measuring probe and a measuring instrument for determining the physical stability of emulsions and dispersions which avoids the aforementioned disadvantages and, in particular, delivers quantifiable results that do not depend on an individual carrying out the measurement; a further object is to provide a suitable measurement method.

The object is achieved by a measuring probe for determining the physical stability of emulsions and dispersions, constructed from a rod comprising a material which is electrically nonconductive at least on the rod surface, which carries at least two conductivity-measurement electrodes separated from one another along the rod, these electrodes being separately supplied with electricity via the interior of the rod at one rod end.

According to another aspect of the invention, a measuring instrument for determining the physical stability of emulsions and disperses includes a measuring probe according to the invention which is arranged vertically in a sample container. An AC voltage is supplied to the conductivity-measurement electrodes, and using a Wheatstone bridge layout, the conductivity for the individual conductivity-measurement electrodes is obtained. A display device displays the results. The measuring instrument may include a computer for controlling measurement display and evaluation of the measurements, and for storing the data obtained. According to still another aspect of the invention, a method for determining the physical stability of emulsions and suspensions includes immersing a memorizing probe according to the invention in a sample container that contains an emulsion or dispersion. The conductivity of the emulsion or dispersion is the measured continuously or at intervals over a given period of time using the conductivity-measurement electrodes may be used to determine and record the time variation of the conductivity difference.

DETAILED DESCRIPTION OF INVENTION

Figure 1A:
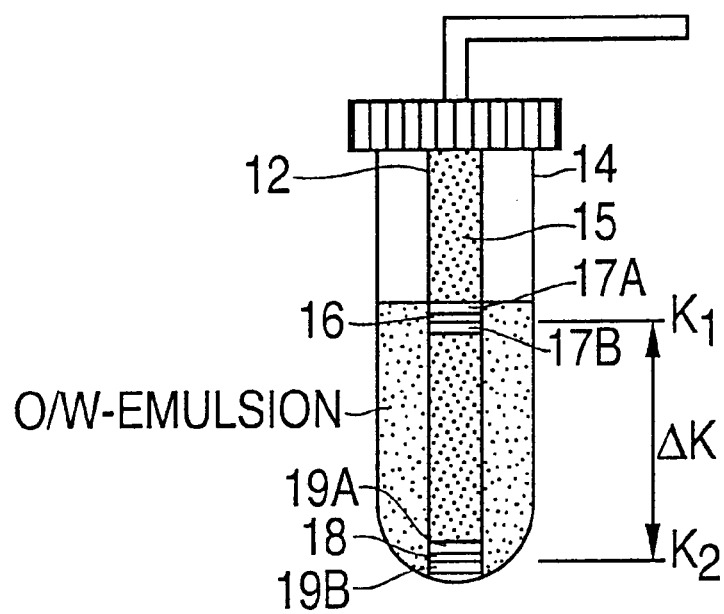
FIG. 1A is a cross-sectional view of a measuring probe in accordance with an embodiment of the invention.

The measurement principle of the measuring probe according to the invention, and of the measuring instrument according to the invention, is based on conductivity measurements in the emulsion or dispersion. They provide a prediction regarding the stability of emulsions and dispersions within a short period, preferably from 4 to 200, particularly preferably from 10 to 100, in particular from 24 to 72 hours after the sample is produced.

The measuring probe and the measuring instrument are suitable, in particular, for determining the physical stability of emulsions and dispersions in which the emulsified or dispersed phase and the emulsifying or dispersing agent have different electrical conductivities. This is the case, in particular, with emulsions and dispersions whose continuous phase is water. As a rule, an organic compound or a mixture containing organic compounds is emulsified or dispersed in such aqueous emulsions and dispersions. The emulsions are, in particular, oil-in-water emulsions. There is not, however, any restriction on the nature of the emulsions and dispersions to be examined.

The conductivity of emulsions and dispersions whose continuous phase is water depends, inter alia, on the concentration of the disperse phase. The conductivity decreases as the concentration of the dispersed phase increases. The relationship can be represented by the following equation:

$$k = A^* \exp(B^* f_i)$$

k=conductivity
$f_i$=concentration of the dispersed phase
A; B=constants

If an emulsion or dispersion is physically unstable, phase separation takes place and continues until the dispersing agent and the previously dispersed phase form two phases. During the phase-separation process, the concentration of the disperse phase changes at the bottom of a storage or sample container and at the surface. The conductivity therefore also changes in these regions.

The invention now provides a measuring probe and a measuring instrument which use special electrodes to determine the conductivity of a colloidal system near the surface and near the bottom of a sample container.

For this purpose, the measuring probe has at least two, and preferably exactly two, conductivity-measurement electrodes which are separated from one another along the rod. These conductivity-measurement electrodes are each preferably formed by two metal rings which are separated from one another, encircle the rod and bear on the surface of the latter, the distances between two conductivity-measurement electrodes along the rod being at least four times as great, preferably at least six times as great as the distances between the two metal rings of a conductivity-measurement electrode.

The distance between the conductivity-measurement electrodes ensures that the conductivity is respectively measured in the vicinity of the measurement electrodes.

The rod is preferably manufactured from an electrically nonconductive plastic as the material. Any desired suitable plastics may be used in this capacity. They should preferably be chemically inert with respect to the emulsions or dispersions to be examined. Besides known thermoplastics, fluorinated polyolefins are preferably used. It is particularly preferable to make the rod from polytetrafluoroethylene (PTFE). It may have a metal core for stiffening. This is advantageous, in particular, when PTFE is used since this material is fairly soft.

The distance between two conductivity-measurement electrodes along the rod may be selected in a wide range depending on the amount of sample to be examined and the geometry of the sample container. The distance between two conductivity-measurement electrodes along the rod is preferably from 1 to 20, particularly preferably from 2 to 10 cm.

The metal rings of the conductivity-measurement electrodes are preferably integrated in the rod so that they do not protrude. The rod then preferably has a continuously smooth surface, which makes it easier to change the sample and to carry out cleaning. Means for positioning the rod in a sample container may optionally be provided at the ends of the rod. For example, the upper and/or lower end of the measuring rod may be thickened so that a defined position is reached during insertion into a sample container.

The measuring probe may have any suitable geometry. It is preferably of essentially cylindrical design, the height of the cylinder being equal to a multiple of the diameter.

Conductivity-measurement probes have until now only been known e.g. from electroplating technology and liquid mensuration. DE-A 197 03 378 relates to a measuring probe for baths having an electrically conductive bath liquid, in particular electroplating baths. The measuring probe is used not only to determine conductivity differences in general, but also to provide protection against running dry and for regulating levels. For instance, it measures the filling depth of an electroplating bath. A temperature sensor may also be provided. The probe may carry a plurality of electrodes which are separated from one another and which can be used to determine various filling depths. A measuring probe for determining the physical stability of emulsions and dispersions is not, however, described.

U.S. Pat. No. 5,212,018 relates to a conductivity-measurement probe which is produced using a special method involving acid treatment of a titanium body. There is no mention that the measuring probe carries at least two conductivity-measurement electrodes which are separated from one another, and no measurement of the physical stability of emulsions and dispersions is described.

The sample container, which encloses the measuring probe according to the invention and holds the emulsion or dispersion to be examined, preferably has an internal volume of from 1 to 150 ml, particularly preferably from 3 to 80 ml. The sample container may be made from any suitable material. It is preferably made from a transparent material, so that the contents of the sample container can be seen from the outside. The sample container is preferably manufactured from a material which is inert with respect to the emulsion or dispersion to be examined. It is particularly preferable to manufacture the sample container from glass.

The measuring probe is supported in the sample container using suitable means, with the proviso that it should also be easy to fill and empty the sample container. For example, the measuring probe may be fastened to the upper end of the preferably cylindrical sample container using a screw thread. This also permits suitable sealing of the sample container, so as to prevent accidental spillage of the emulsion or dispersion. Electricity may then be supplied to the conductivity-measurement electrodes via this screw cap, and suitable plug connectors or screw connectors may be provided for the electrical connection.

The sample container or the measuring probe may in this case have suitable devices to position the measuring probe.

Figure 1B:
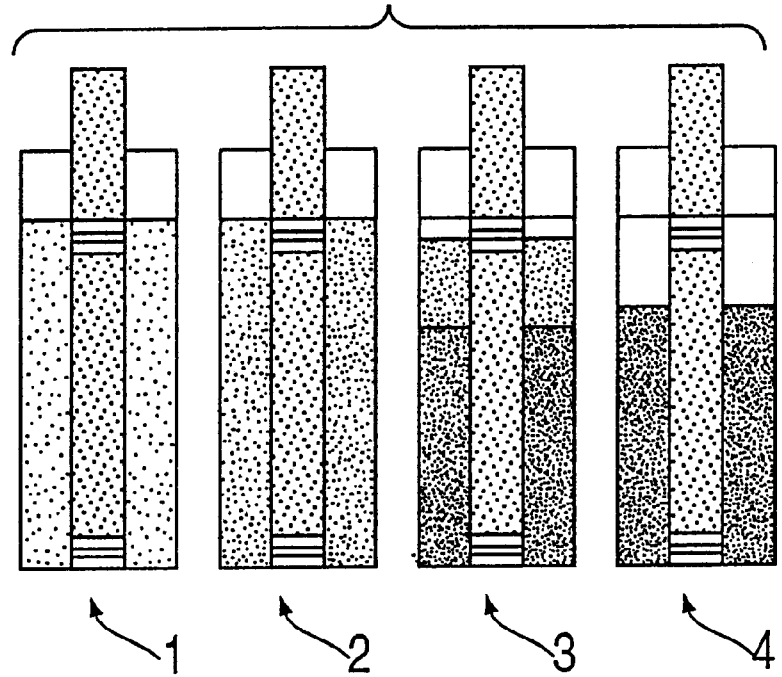
FIG. 1B is a cross-sectional view of four measuring probes and sample containers in accordance with an embodiment of the invention.
Figure 2:
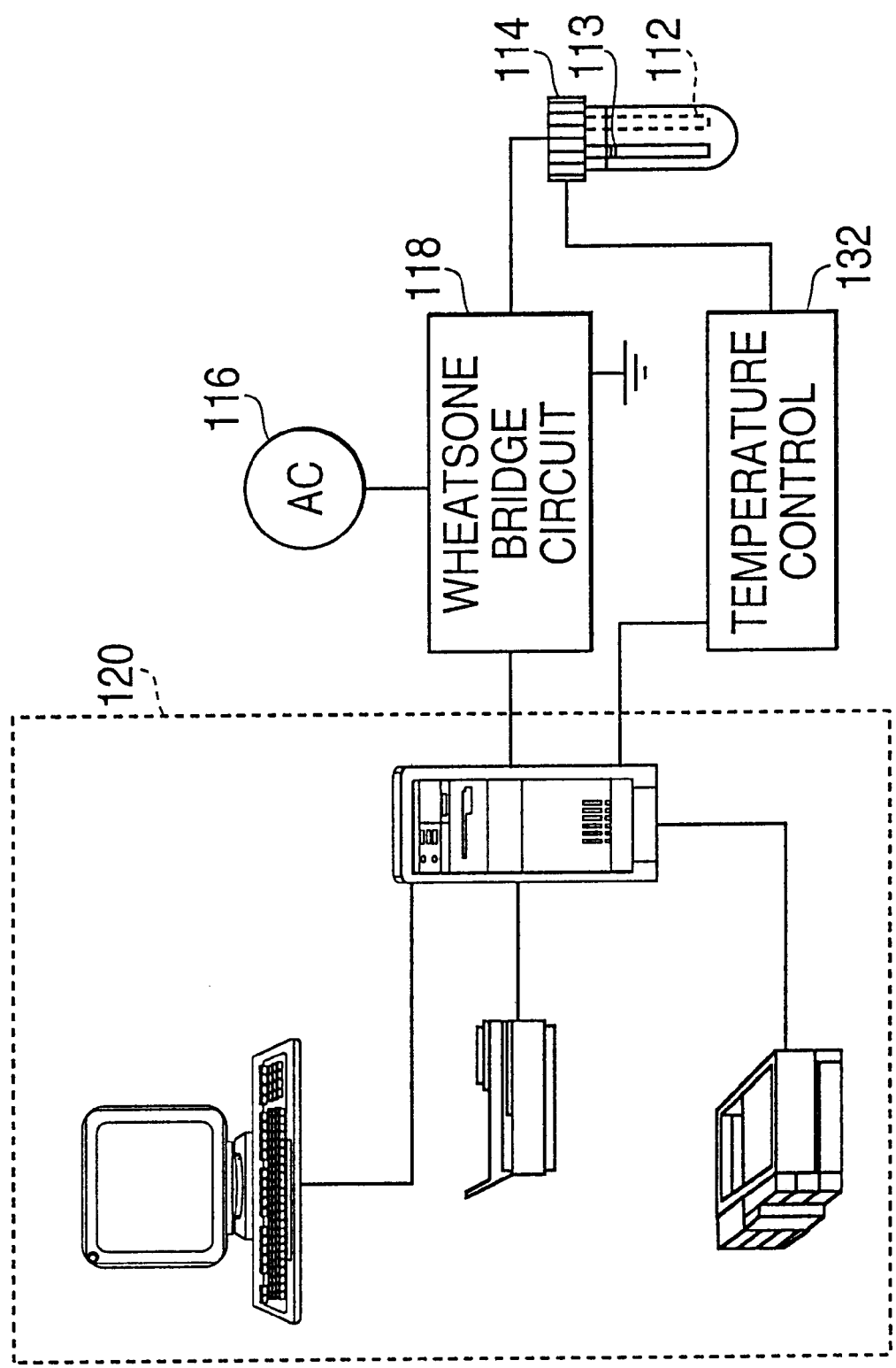
FIG. 2 is a block diagram illustrating a measurement instrument in accordance with an embodiment of the invention.

The measuring probe according to the invention and the measurement principle according to the invention are explained in more detail in FIGS. 1 and 2 of the drawing.

FIG. 1A shows a cross section of a measuring probe 12 according to the invention with the sample container 14. The elongate measuring probe 12 has two conductivity-measurement electrodes 16, 18, which are located respectively on a rod 15 at the positions denoted by $K_1$ and $K_2$. The sample container 14 is filled with an oil-in-water (O/W) emulsion. As shown, the conductivity-measurement electrodes 16, 18 each comprise two metal rings (17A, 17B and 19A, 19B), which are used to determine conductivities $K_1$ and $K_2$ in the surface region and in the bottom region of the sample container, from which a conductivity difference $\Delta K$ may be calculated. For its part, FIG. 1B represents cross-sectional views of four measuring probes and sample containers according to the invention. The measurement principle will be explained here with reference to phase separation.

1: At this stage, the system is homogeneous and there is no perceptible difference in the concentration of the disperse phase between the surface of the emulsion and the cell bottom. The conductivity difference ($\Delta K$) between these two measurement points is therefore also zero, and the system can be regarded as stable.

2: At this stage, an invisible "creaming effect" takes place, which is due to a change in the concentration of the disperse phase at the surface and at the cell bottom, and which therefore leads to a difference in the conductivity. By virtue of the sensitive electrodes, this conductivity difference can be detected long before any phase separation can be observed with the naked eye.

3: As the creaming continuous, the difference between the conductivities experiences a pronounced increase. Only now can an experienced observer identify any phase segregation with the naked eye.

4: At the final stage, the conductivity difference becomes a maximum and complete phase segregation of the emulsion can be seen, for example into an oil phase and an aqueous phase.

The decisive advantage of the measuring probe according to the invention and of the measuring instrument according to the invention is that it is not necessary to wait for visible phase segregation before determining that emulsions and dispersions are physically unstable. The increase in the conductivity difference within the sample at stage (2) is a reliable parameter for predicting the physical stability of a colloidal system.

The invention also relates to a measuring instrument 100 for determining the physical stability of emulsions and dispersions. As shown in FIG. 2, one such instrument is constructed from at least one measuring probe 112 and a sample container 114, as they are defined above, the measuring probe 112 being arranged essentially vertical in the sample container 114, an AC voltage supply 116 for the conductivity-measurement electrodes, which supplies the conductivity-measurement electrodes with AC voltage according to a Wheatstone bridge layout 118 and measures the conductivity for the individual conductivity-measurement electrodes, and a display device for the conductivity of the individual conductivity measurement electrodes.

The Wheatstone bridge circuit is represented in FIG. 2 by box 132. It will be appreciated, of course, that the conductivity-measurement electrode(s) form a part of that circuit. Suitable AC Wheatstone bridges for measuring the conductivity of electrolytes are known. The basic underlying circuit and the measurement system are described, for example, in Walter J. Moore, Physikalische Chemie, $4^{th}$ edition, 1986, pages 510 to 512 (Walter de Gruyter & Co). There is therefore no need for further discussion of the special structure of the circuit here.

Preferably, the measuring instrument 100 according to the invention furthermore has a computer 120 for driving the conductivity-measurement electrodes, for displaying and optionally evaluating the measured conductivities, and optionally for storing the data or measurements obtained.

Suitable computers are known, and are extensively used for driving electrical and electronic instruments. They preferably consist of a central processing unit, an input keyboard, a monitor, an electronic storage medium, such as a hard disk, floppy disk or CD-ROM, and optionally a printer or plotter as illustrated in FIG. 2.

The measuring instrument is preferably designed in such a way that a plurality of measuring probes can be operated in parallel, so that a plurality of measurements, preferably from two to twenty, in particular from two to ten, can be carried out in parallel. One such optimal plurality of probes 113 is represented with dashed lines in FIG. 2. Preferably, the measuring instrument furthermore has a device (illustrated generally as element 130) for controlling the temperature of the measuring probe(s). While the device 130 is shown functionally in relation to the container, the device 130 may, for example, involve a suitably dimensioned cryostat which can be used to cool or warm the samples, and to run temperature programmes. The temperature control device 130 may in this case likewise be supervised using the computer 120.

FIGS. 3A–3D represents typical measurement results for a physically unstable emulsion. In each case, the conductivity is plotted against time. The procedure was carried out with one measuring probe having two conductivity-measurement electrodes, respectively in the surface and bottom regions of a sample container.

Figure 3A:
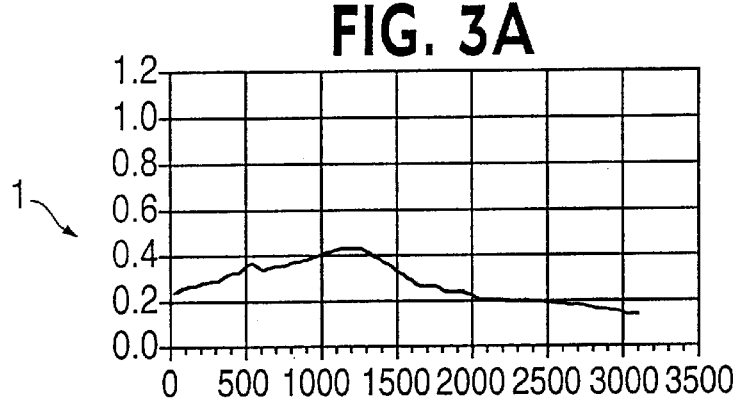
FIG. 3A is a graph showing a conductivity profile for an upper conductivity-measurement electrode according to an embodiment of the invention.
Figure 3B:
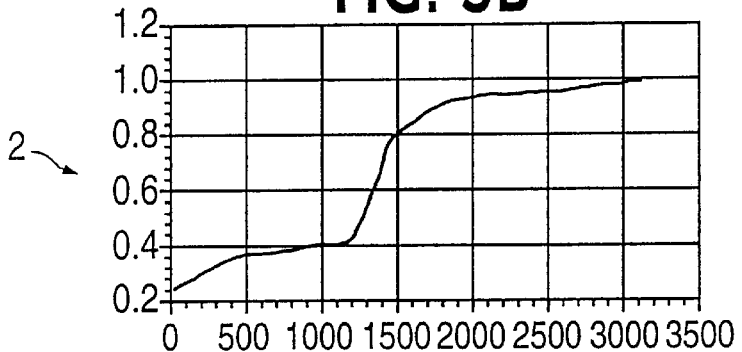
FIG. 3B is a graph showing a conductivity profile for a lower conductivity-measurement dectectrade according to an embodiment of the invention.
Figure 3C:
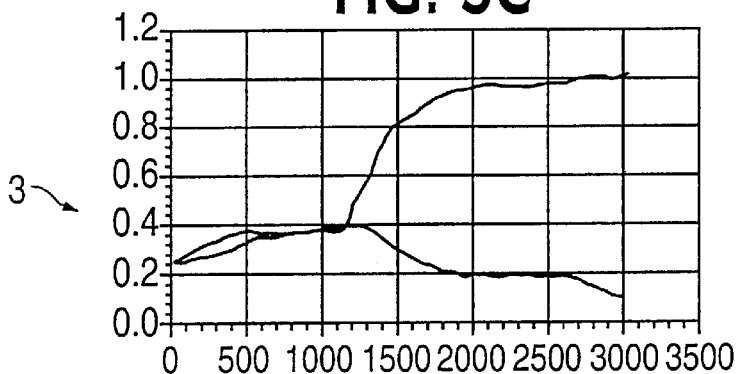
FIG. 3C is a graph showing a plot of the curves of FIGS. 3A and 3B.
Figure 3D:
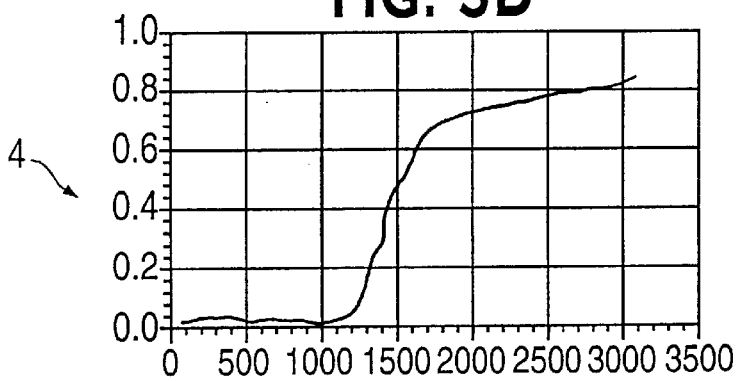
FIG. 3D is a graph showing the difference between the curves of FIGS. 3A and 3B.

The first graph of FIG. 3A shows the conductivity profile for the upper conductivity measurement electrode. The second graph of FIG. 3B shows the conductivity profile for the lower measuring probe. The two curves are plotted together in the third graph of FIG. 3C. The fourth graph of FIG. 3D represents the difference between the graph of FIG. 3B and graph of FIG. 3A. In particular, the difference represented in the graph of FIG. 3D clearly demonstrates that phase separation occurs after about 1200 minutes.

The measuring instrument according to the invention is universally usable and delivers reliable stability predictions in a few hours, in particular for O/W emulsions, gels and aqueous dispersions.

The emulsion or dispersion to be examined preferably has a minimum electrical conductivity of 100 $\mu$S/cm.

The measurement range of the temperature-dependent conductivity measurements is preferably between $-20$ and $80°$ C. for the temperature, and between 100 $\mu$S/cm and 2000 $\mu$S/cm for the conductivity (corresponding to a voltage of from 0.1 to 8.5 V). Sample sizes in the range of from 5 to 10 ml are especially suitable. The measuring instrument is preferably operated using standard 220/240 VAC 50/60 Hz mains voltage.

The measuring instrument according to the invention has, inter alia, the following advantages over the known visual assessment of emulsions and dispersions:

the stability data can be ascertained at least 30 times faster a plurality of different samples can be surveyed at the same time stability data are recorded continuously the critical temperature for emulsions and dispersions, above which instabilities occur, can be determined easily and reproducibly.

The invention also relates to a method for determining the physical stability of emulsions and dispersions, in which an emulsion or dispersion is placed in a sample container, a measuring probe as described above is immersed in the filled sample container, and the conductivity of the emulsion or dispersion is measured continuously or at intervals over a given period of time using the conductivity-measurement electrodes. Preferably, the time variation of the conductivity difference is determined and recorded using at least two conductivity-measurement electrodes. It is particularly preferable to carry out the method as described in detail above.

What is claimed is:

1. Measuring instrument for determining the physical stability of emulsions and dispersions, comprising:

at least one measuring probe for determining the physical stability of emulsions and dispersions, said measuring probe including:
 a rod comprised of a material which is electrically nonconductive at least on the rod surface; and
 at least two conductivity-measurement electrodes separated from one another along the rod, each electrode being separately supplied with electricity via the interior of the rod at one end of the rod;
 a sample container adapted to hold the emulsion or dispersion to be examined, wherein the at least one measuring probe is arranged vertically in the sample container; and
a supply that supplies the conductivity-measurement electrodes with AC voltage using a Wheatstone bridge layout to thereby measure the conductivity for the individual conductivity-measurement electrodes.

2. Measuring instrument according to claim 1, wherein the conductivity-measurement electrodes are each formed by two metal rings which are separated from one another, encircle the rod and bear on the surface of the rod.

3. Measuring instrument according to claim 2, wherein the distances between two conductivity-measurement electrodes along the rod is at least four times as great as the distance between the two metal rings.

4. Measuring instrument according to claim 3, wherein the distances between two conductivity-measurement electrodes along the rod is at least six times as great as the distance between the two metal rings.

5. Measuring instrument according to claim 1, wherein the rod is made from an electrically nonconductive plastic.

6. Measuring instrument according to claim 5, wherein the rod is made from PTFE.

7. Measuring instrument according to claim 5, wherein the rod includes a metal core for stiffening.

8. Measuring instrument according to claim 1, wherein the distance between two conductivity-measurement electrodes along the rod is from 1 to 20 cm.

9. Measuring instrument according to claim 8, wherein the distance between two conductivity-measurement electrodes along the rod is from 2 to 10 cm.

10. Measuring instrument according to claim 1, wherein the sample container has an internal volume of from 5 to 150 ml.

11. Measuring instrument according to claim 10, wherein the sample container has an internal volume of from 20 to 80 ml.

12. Measuring instrument according to claim 1, further comprising a display device adapted to display measurements of the conductivity of the individual conductivity-measurement electrodes.

13. Measuring instrument according to claim 1, further comprising a computer that drives the conductivity-measurement electrodes and displays the conductivity of the conductivity-measurement electrodes.

14. Measuring instrument according to claim 13, wherein the computer is adapted to evaluate the conductivity of the conductivity-measurement electrodes and store data that is obtained.

15. Measuring instrument according to claim 13, further comprising a device for controlling the temperature of the at least one measuring probe.

16. Measuring instrument according to claim 1, wherein the emulsion is an oil-in-water emulsion.

17. Method for determining the physical stability of emulsions or suspensions in a sample container, comprising:

providing a measuring probe, said measuring probe including: a rod comprised of a material which is electrically nonconductive at least on the rod surface; and at least two conductivity-measurement electrodes separated from one another along the rod, each electrode being separately supplied with electricity via the interior of the rod at one end of the rod;

immersing the measuring probe in the sample container, and measuring the conductivity of the emulsion or dispersion continuously or at intervals over a given period of time using the conductivity-measurement electrode;

wherein a time variation of a difference in conductivity between the at least two conductivity-measurement electrodes is determined and recorded.

* * * * *